(12) United States Patent
Matsuyama

(10) Patent No.: US 8,784,803 B2
(45) Date of Patent: Jul. 22, 2014

(54) THERAPEUTIC AGENT FOR LIVER-RELATED DISEASES

(75) Inventor: Akifumi Matsuyama, Kobe (JP)

(73) Assignee: Osaka Air Machine Service, Ltd., Higashiosaka (JP)

( * ) Notice: Subject to any disclaimer, the term of this patent is extended or adjusted under 35 U.S.C. 154(b) by 0 days.

(21) Appl. No.: 13/393,023

(22) PCT Filed: Aug. 27, 2010

(86) PCT No.: PCT/JP2010/064623
§ 371 (c)(1),
(2), (4) Date: Feb. 28, 2012

(87) PCT Pub. No.: WO2011/024962
PCT Pub. Date: Mar. 3, 2011

(65) Prior Publication Data
US 2012/0156181 A1  Jun. 21, 2012

(30) Foreign Application Priority Data
Aug. 28, 2009  (JP) ................................. 2009-198166

(51) Int. Cl.
*A01N 63/00* (2006.01)
*C12N 5/00* (2006.01)

(52) U.S. Cl.
USPC ........................................ 424/93.7; 435/325

(58) Field of Classification Search
USPC .......................................... 424/93.7; 435/325
See application file for complete search history.

(56) References Cited

U.S. PATENT DOCUMENTS

| | | | |
|---|---|---|---|
| 6,355,239 B1 * | 3/2002 | Bruder et al. | 424/93.1 |
| 2003/0082152 A1 * | 5/2003 | Hedrick et al. | 424/93.21 |
| 2004/0097867 A1 * | 5/2004 | Fraser et al. | 604/27 |
| 2007/0197440 A1 * | 8/2007 | Grancha Gamon et al. | 514/12 |
| 2007/0249045 A1 | 10/2007 | Gimble et al. | |
| 2010/0151574 A1 | 6/2010 | Matsuyama et al. | |
| 2010/0183568 A1 | 7/2010 | Matsuyama et al. | |

FOREIGN PATENT DOCUMENTS

| | | |
|---|---|---|
| EP | 2166084 A1 | 3/2010 |
| WO | WO 2008/153179 A1 | 12/2008 |
| WO | WO 2008/153180 A1 | 12/2008 |

OTHER PUBLICATIONS

Zuk et al. Human Adipose Tissue is a Source of Multipotent Stem Cells; Molecular Biology of the Cell, vol. 13 (2002) pp. 4279-4295.*
Morizono et al. Multilineage Cells From Adipose Tissue as Gene Delivery Vehicles; Human Gene Therapy, vol. 14 (2003) pp. 59-66.*
Stewart et al. Methylcellulose Protects the Ability of Anchorage-Dependent Cells to Adhere Following Isolation and Holding in Suspension; Biotechniques, vol. 19, No. 4 (1995) pp. 598-604.*
Mutin et al. Reevaluation of Trypsin-EDTA for Endothelial Cell Detachment Before Flow Cytometry Analysis; Endothelium, vol. 4 (1996) pp. 289-295.*
Seo, M.J. et al.;"Differentiation of human adipose stromal cells into hepatic lineage in vitro and in vivo";Biochemical and Biophysical Research Communications; vol. 328, No. 4, pp. 258-264 (2005).
Tan, G. et al.;"Therapeutic effect of adipose tissue-derived mesenchymal stem cells transplantation on rat model of hepatic cirrhosis";Shijie Huaren Xiaohua Zazhi; vol. 17, No. 11, pp. 1074 -1078 (Apr. 2009).
Wang, X. et al.;"Treatment of CCl4 induced chronic liver injury with rat adipose tissue-derived mesenchymal stem cells";Weichangbingxue He Ganbingxue Zazhi;vol. 18, No. 9, pp. 791-794 (Sep. 2009).
Hanayuki Okura et al.;"Hito Shibo Soshiki Kansaibo Yurai Kanshoyo-yo Saibokai o Mochiita Kazokusei ko Cholesterol Kessho ni Taisuru Shinki Chiryoho Kaihatsu"; Regenerative Medicine;vol. 9, p. 303 (2010).
Parker A M et al:"Adipose-derived stem cells for the regeneration of damaged tissues", Expert Opinion on Biological Therapy, Jan. 2006, pp. 567-578, vol. 6, No. 6, Ashley, London, GB.

* cited by examiner

*Primary Examiner* — Susan Hanley
*Assistant Examiner* — Paul Martin
(74) *Attorney, Agent, or Firm* — Marvin A. Motsenbocker; Mots Law, PLLC

(57) ABSTRACT

The present invention relates to a therapeutic agent for liver-related diseases, comprising adipose tissue-derived multilineage progenitor cells; and others.

5 Claims, 5 Drawing Sheets

THERAPEUTIC AGENT FOR LIVER-RELATED DISEASES

TECHNICAL FIELD

The present invention relates to a therapeutic agent for treating a liver-related disease, which includes adipose tissue-derived multilineage progenitor cells (referred to hereinafter as "ADMPCs"), and others.

The present application claims priority on Japanese Patent Application No. 2009-198166 filed on Aug. 28, 2009, the disclosure of which is incorporated by reference herein

BACKGROUND ART

Hereditary disorders, such as hemophilia and familial hypercholesterolemia, are representative of refractory diseases, many therapies for which only control worsening of patients' conditions using symptomatic treatments. For example, hemophilia is a hereditary disorder which results from mutations in genes coding for blood coagulation factors expressed in the liver, such as factor VIII or IX, and is treated with treatments administered from outside the body which compensate for these defect factors. However, patient's own immune responses may elicit circulating anti-coagulation factors, leading to discontinuing these treatments.

On the other hand, familial hypercholesterolemia (FH) is a hereditary disorder due to deficiency of the LDL (low-density lipoprotein) receptor expressed in the liver. In homozygotic patients, cholesterol-lowing drugs such as statins have no effects against the disorder. FH patients are required to reduce the value of cholesterol in the blood by periodic dialysis, which dialysis causes a great deal of physical and economic burdens and cannot inhibit the progression of arteriosclerosis.

As therapies for these disorders caused by decreased or lost functions of liver cells, liver transplantation or implantation of liver cells isolated from healthy individuals has been used, but these are not generally used yet, because of the problem of shortage of donors and heavy physical burdens on patients. On the other hand, remarkable developments in regenerative therapies using regenerative medicine, cell/tissue engineering, genetic engineering, and the like provide the path to conquer refractory diseases. As sources of cellular materials employed in these regenerative therapies, attention has been attracted to adult stem cells derived from mesenchymal tissues, in particular, somatic stem cells derived from adipose tissues which can be harvested with safety and ease and propagated in culture. However, in order to achieve the induction of differentiation of these stem cells to particular tissues or cells and their culturing outside the body, huge amounts of cost and labor are required, and thus there remain problems to be solved.

It has been reported by Seo et al. group that the implantation of adipose-derived mesenchymal stem cells in the liver resulted in their differentiation into hepatocytes (Non-Patent Document 1). Similar reports presume that from the fact that non-human stem cells derived from adipose tissues can engraft in the liver and are positive for albumin in immuno-histological characterization, these stem cells have been differentiation-induced into hepatocytes in regional sites. However, it is unclear whether or not the hepatocytes reported to be differentiated and to engraft are active, and a problem arises that the number of engrafted cells is significantly small.

PRIOR ART DOCUMENTS

Non-Patent Documents

Non-Patent Document 1: M. J. Seo et al., Biochemical and Biophysical Research Communications, 328, (2005), 258-264

DISCLOSURE OF THE INVENTION

Problems to be Solved by the Invention

In view of the above-described situations, the inventors have devoted themselves to research, in order to develop a method for engrafting, in the liver with higher efficiency, mesenchymal stem cells introduced from outside the body. The inventors found that when adipose tissue-derived multilineage progenitor cells, which were developed by the inventors of the present application (see, International Publication No. WO 2008/15317 Pamphlet), were administered via portal vein, high rates of their engraftment in the liver and efficient their differentiation into hepatocytes were accomplished, thereby leading to the completion of the present invention.

Means for Solving the Problems

Therefore, the present invention is directed to:
(1) a therapeutic agent for treating a liver-related disease, including adipose tissue-derived multilineage progenitor cells;
(2) the therapeutic agent according to (1), wherein the adipose tissue-derived multilineage progenitor cells are a population of cells obtained by:
(a) removing erythrocytes from a population of adipose tissue-derived cells, thereby to form a population of preadipose tissue-derived multilineage progenitor cells;
(b) culturing the resultant population of the preadipose tissue-derived multilineage progenitor cells;
(c) removing cells other than the adipose tissue-derived multilineage progenitor cells from the cultured population of the preadipose tissue-derived multilineage progenitor cells;
(3) the therapeutic agent according to (1) or (2), wherein the agent is administered via portal vein;
(4) the therapeutic agent according to any one of (1) to (3), wherein the liver-related disease is non-inflammatory;
(5) the therapeutic agent according to any one of (1) to (3), wherein the liver-related disease is selected from blood coagulation disorders, metabolic diseases, and liver diseases;
(6) the therapeutic agent according to (4) or (5), wherein the liver-related disease is hemophilia or familial hypercholesterolemia;
(7) a method for treating a liver-related disease, which includes administering adipose tissue-derived multilineage progenitor cells to a subject; and
(8) an adipose tissue-derived multilineage progenitor cell for use in treating a liver-related disease.

Effects of the Invention

The present invention can provide, for example, a therapeutic agent for treating a liver-related disease, which includes adipose tissue-derived multilineage progenitor cells that exhibit their increased engraftment and differentiation in the liver when introduced into the body. According to the present invention, there can be achieved an excellent effect that when compared to prior or existing methods, hepatocytes of a patient can be replaced at high rates with hepatocytes derived from the adipose tissue-derived multilineage progenitor cells, and also the replaced hepatocytes work in an integrated manner with the hepatic parenchyma of the recipient via cell contact.

BRIEF DESCRIPTION OF THE DRAWINGS

FIG. 2(B) is a magnified representation of the peak in FIG. 2(A). In the graph, the ordinate axis represents relative values of serum cholesterol.

EMBODIMENTS FOR CARRYING OUT THE INVENTION

Figure 1:
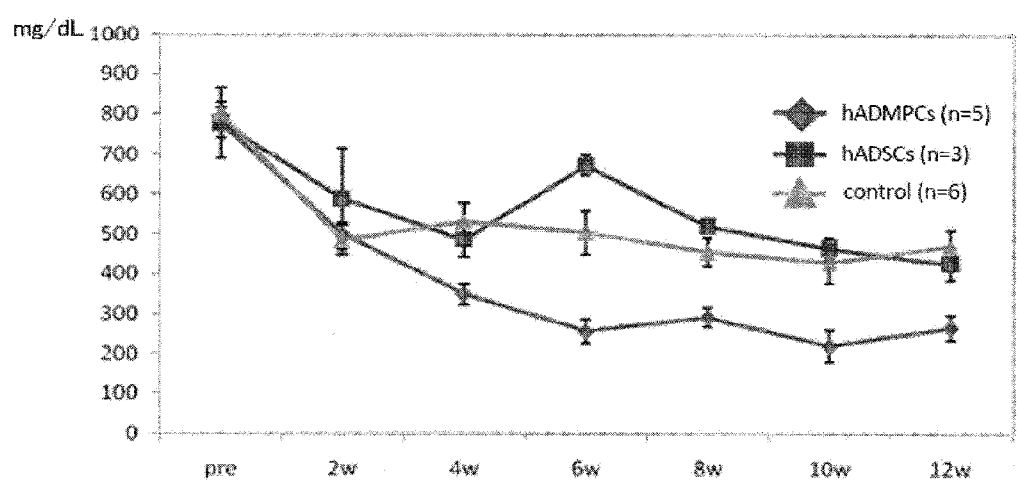
FIG. 1 shows changes in total serum cholesterol in a group implanted with hADMPCs (hADMPC), a group implanted with hADSCs (according to a method of Zuk et al.), and a group with no implantation (saline control). In the graph, the abscissa axis represents elapsed days and the ordinate axis represents values of total serum cholesterol.

The present invention, in one aspect, is directed to a therapeutic agent for treating a liver-related disease, including adipose tissue-derived multilineage progenitor cells. As used herein, adipose tissue-derived multilineage progenitor cells refer to cells which are capable of differentiation into different cell lineages of the endoderm, mesoderm, and ectoderm and express undifferentiation makers, Islet-1 and/or GATA-4. Adipose tissue-derived multilineage progenitor cells as described herein can be obtained by differentiation from embryonic stem cells and the like, besides adipose tissues. The species of animals from which adipose tissue-derived multilineage progenitor cells as described herein are derived is not particularly limited, but preferably includes, for example, mammals, including humans, mice, rats, rabbits, dogs, cats, bovines, horses, monkeys, and others, more preferably humans. It is preferable that the species of animals from which adipose tissue-derived multilineage progenitor cells as described herein are derived is the same species as that of a subject to be treated according to the present invention, or is a subject to be treated according to the present invention.

Adipose tissue-derived multilineage progenitor cells which are used in the present invention refer to a population of cells which has low contents of undesirable contaminations, for example, cells other than adipose tissue-derived multilineage progenitor cells, such as erythrocytes and vascular endothelial cells, and thus have the advantages of easy culturing, increased differentiation efficiency, and others. Procedures for removing these contaminants include, for example, procedures or methods using differences in specific gravity from the adipose tissue-derived multilineage progenitor cells, for example, methods based on specific gravity; procedures or methods using differences in adhesion property from the adipose tissue-derived multilineage progenitor cells, for example, methods using chelating agents such as EDTA or enzymes such as trypsin; antigen-antibody methods, such as sorting, MACA; methods based on morphological selection; single cell cloning; and methods based on hemolysis. Reduced contaminants in the population of cells may be ascertained visually under microscopes, or alternatively with flow cytometry, immunohistological staining, or others, for example, by quantitative determination of contaminants' makers using RT-PCR, ELISA, and other methods.

A population of cells which is used in the present invention includes at least 20% or more, preferably 30%, 40%, 50%, 60%, 700, 75%, 80%, 850, 900, 93%, 960, 97%, 980, or 99%, of adipose tissue-derived multilineage progenitor cells. Since adipose tissue-derived multilineage progenitor cells are included at the percentages mentioned above, a population of cells which is used in the present invention has the advantages of easy maintaining of the adipose tissue-derived multilineage progenitor cells and of providing increased efficiency upon differentiation, for example. A population of cells which is used in the present invention may include, in addition to the adipose tissue-derived multilineage progenitor cells, cells, like feeder cells, which are effective for maintaining or differentiation of the adipose tissue-derived multilineage progenitor cells, vascular endothelial cells, fibroblast cells, and the others. Inclusion of these cells will allow the above-mentioned advantages to be enhanced.

Adipose tissue-derived multilineage progenitor cells which are used in the present invention may be, for example, a population of cells obtained by: (a) removing erythrocytes from a population of adipose tissue-derived cells, thereby to obtain a population of preadipose tissue-derived multilineage progenitor cells; then (b) culturing the resultant population of the preadipose tissue-derived multilineage progenitor cells; (c) removing cells other than the adipose tissue-derived multilineage progenitor cells from the cultured population of the preadipose tissue-derived multilineage progenitor cells. In the present invention, these steps may be carried out sequentially or in parallel. The adipose tissues which are used in this aspect of the present invention may be any of subcutaneous adipose tissues and visceral adipose tissues within a living body. In addition, the species of animals from which the adipose tissues are derived is not particularly limited, but preferably includes, for example, mammals, including humans, mice, rats, rabbits, dogs, cats, bovines, horses, monkeys, and others, more preferably humans. Alternatively, it is preferable that the species of animals from which the adipose tissues are derived is the same species as that of a subject to be treated according to the present invention, or is a subject to be treated according to the present invention.

A population of adipose tissue-derived cells which is used in the present invention refers to a population of cells including at least adipose tissue-derived multilineage progenitor cells. The population of adipose tissue-derived cells may include erythrocytes, vascular endothelial cells, fibroblast cells, and others, in addition to the adipose tissue-derived multilineage progenitor cells. The population of adipose tissue-derived cells can be obtained, for example, by treating an adipose tissue with an enzyme such as collagenase, or physical procedure or method, and/or removing lipids and others, for example, with centrifugation, filter processing, or the like.

Erythrocytes have the property of adsorbing adipose tissue-derived multilineage progenitor cells, which property may cause their decreased yields. Therefore, it is necessary to remove erythrocytes from a population of adipose tissue-derived cells. Removing of erythrocytes from a population of adipose tissue-derived cells may be carried out by any procedures or methods, for example, by procedures or methods other than those relying on the difference in adhesion property between erythrocytes and the other cells. Preferably, such removing can be effected by methods based on specific gravity, methods based on hemolysis, methods using filters, more preferably methods based on specific gravity. Methods based on specific gravity can be carried out using specific-gravity solutions of appropriate specific gravities, for example, commercially available specific-gravity solutions, such as Lymphoprep (manufactured by Nycomed). The specific gravity of specific-gravity solutions used may be between those of erythrocytes and the other cells, preferably from 1.063 to 1.119, more preferably from 1.070 to 1.110, most preferably 1.077.

As used in the specification, a population of preadipose tissue-derived multilineage progenitor cells refers to a population of cells including at least adipose tissue-derived multilineage progenitor cells. The population of preadipose tissue-derived multilineage progenitor cells may include erythrocytes, vascular endothelial cells, fibroblast cells, and others, in addition to the adipose tissue-derived multilineage progenitor cells. As described above, the population of preadipose tissue-derived multilineage progenitor cells is substantially free of erythrocytes. Removing erythrocytes, thereby to form a population of preadipose tissue-derived multilineage progenitor cells, will make it possible to carry out with great ease and high efficiency the subsequent removal of cells other than the adipose tissue-derived multilineage progenitor cells.

In the present invention, it is preferable that a population of preadipose tissue-derived multilineage progenitor cells is cultured in adhesion culture, from the viewpoints of maintaining these cells in their undifferentiated state and of carrying out efficient removal, as described below, of cells other than the adipose tissue-derived multilineage progenitor cells. Adhesion culture may be performed by known procedures, for example, using such as dishes, flasks, roller bottles or spinner flasks. In addition, it is preferable, from the viewpoint of carrying out efficient removal of cells other than the adipose tissue-derived multilineage progenitor cells, that a population of preadipose tissue-derived multilineage progenitor cells is cultured for a sufficient period of time so that cells, such as blood endothelial cells, fibroblast cells, and others, which are contained in the cell population, are allowed to adhere well onto contacting surfaces of culturing vessels. For example, a population of preadipose tissue-derived multilineage progenitor cells can be cultured for a period of 12 to 48 hours, preferably 12 to 36 hours.

In the specification, cells other than the adipose tissue-derived multilineage progenitor cells refer to, for example, adhesive cells, such as blood endothelial cells, fibroblast cells, and others. Removing of cells other than the adipose tissue-derived multilineage progenitor cells from a population of preadipose tissue-derived multilineage progenitor cells may be carried out by any procedures or methods, preferably using substances other than trypsin, more preferably chelating agents such as EDTA and EGTA, most preferably EDTA. Preferably, such removing is based on the difference in adhesion property between the adipose tissue-derived multilineage progenitor cells and the other cells. Besides the above, it is possible to remove cells other than the adipose tissue-derived multilineage progenitor cells, for example, by filtration through filters. Removal of these other cells will increase the purity and yield of adipose tissue-derived multilineage progenitor cells which are obtained.

In the present invention, adipose tissue-derived multilineage progenitor cells as described herein may be used, for example, for therapeutic agents as described below, by employing directly a population of cells which is obtained by removing cells other than the adipose tissue-derived multilineage progenitor cells from a population of preadipose tissue-derived multilineage progenitor cells, or alternatively after expansion culturing the obtained population of cells. Such expansion culturing may be performed not only after removing cells other than the adipose tissue-derived multilineage progenitor cells from a population of preadipose tissue-derived multilineage progenitor cells, but during the course of preparing adipose tissue-derived multilineage progenitor cells from an adipose tissue. Expansion culturing is preferably performed in adhesion culture. In addition, the resulting population of cells may be used for therapeutic agents, for example, after freezing and thawing in the presence of an appropriate cryoprotectant or the like.

In the present invention, dosage forms of the above-mentioned therapeutic agents are not particularly limited, but preferably are in the form of cell suspensions. Adipose tissue-derived multilineage progenitor cells as described herein may be suspended in appropriate solutions, such as Ringer solution, to prepare therapeutic agents. Alternatively, cell suspensions which have been frozen in the presence of an appropriate cryoprotectant or the like may be thawed and used as therapeutic agents. In these therapeutic agents, cell concentrations preferably are $1.\text{times}.10.\sup.5$ cells/mL or higher. An therapeutic agent of the present invention may further include, in addition to the adipose tissue-derived multilineage progenitor cells, substances which will promote engraftment of the adipose tissue-derived multilineage progenitor cells in the liver, such as heparin or hyaluronic acid, liver function improving agents, such as HMG-CoA reductase inhibitors (such as Mevalotin), fibrates (such as Bezatol), bile acid adsorbents (such as cholestyramine) or bile acid absorption inhibitors (such as ZETIA™), and appropriate additives, excipients, and others.

A therapeutic agent of the present invention is preferably applied parenterally, and may be administered, for example, via portal vein, via vein, via artery, or via bile duct. From the viewpoint of achieving high-efficiency differentiation and engraftment in the liver, it is preferable that a therapeutic agent of the present invention is administered via portal vein. Administration of a therapeutic agent of the present invention via portal vein can achieve an excellent effect that when compared to prior or existing methods, hepatocytes of a patient can be replaced at high rates with hepatocytes derived from the adipose tissue-derived multilineage progenitor cells, and also the replaced hepatocytes work in an integrated manner with the hepatic parenchyma of the recipient via cell contact. The dosage amount, frequency of administration, and number of administrations, etc. of a therapeutic agent of the present invention are selected as appropriate, depending upon various factors, such as the condition of a subject to be treated and the severity of the disease. For example, the dosage amount of a therapeutic agent of the present invention may be about $2.5 \times 10^6$ cells per kg of body weight or more, preferably about $1.0 \times 10^7$ cells per kg of body weight or more, and more preferably about $1.5 \times 10^7$ cells per kg of body weight or more. The subject may be any subjects, for example, human subjects or alternatively non-human subjects such as mammal subjects, such as mice and monkeys.

In the present invention, adipose tissue-derived multilineage progenitor cells as described herein may be used by attaching them onto, adhering them onto, or containing them in supports. For example, a cell sheet may be implanted in the liver, in which cases the cell sheet is constructed by attaching adipose tissue-derived multilineage progenitor cells as described herein onto a sheet support, by adhering adipose tissue-derived multilineage progenitor cells as described herein onto a sheet support, or by containing adipose tissue-derived multilineage progenitor cells as described herein in a sheet support. In cases where a therapeutic agent of the present invention is formed into a cell sheet as appropriate, the size and thickness of the sheet, and the number of cells contained in the sheet may be selected as appropriate, depending upon various factors, such as the condition of a subject to be treated and the severity of the disease. The cells may be contained in a cell sheet in either single-layered or multilayered form. In addition, shapes and materials of supports which can be used for cell sheets of the present invention can be determined as appropriate according to common technical knowledge in the art. Among materials of supports which can be used for cell sheets of the present invention are, for example, hyaluronic acid sponges and methyl cellulose sponges. These cell sheets may further include, in addition to the adipose tissue-derived multilineage progenitor cells, for example, phosphate buffered saline (PBS), medium, substances which will promote engraftment of the adipose tissue-derived multilineage progenitor cells in the liver, such as heparin or hyaluronic acid, liver function improving agents, such as HMG-CoA reductase inhibitors (such as Mevalotin), fibrates (such as Bezatol), bile acid adsorbents (such as cholestyramine) or bile acid absorption inhibitors (such as ZETIA™), and others. Forms of cell sheets will make it easier to deal with the cells, for example, when used for implantation. These cell sheets may be implanted as appropriate, depending upon the condition of a subject to be implanted with a cell sheet, the severity of the disease, and others. The subject may be any subjects, for example, human subjects or alternatively non-human subjects such as mammal subjects, such as mice and monkeys.

A liver-related disease which is indented by the present invention refers to a disease resulting from decreased liver function. Diseases resulting from decreased liver function include diseases which result not only from decreased function, but from impaired function, of the liver or of hepatocytes, for example, liver diseases such as hepatitis, hepatic cirrhosis, liver cancer, and hepatic failure; drug-induced liver injuries; alcoholic liver injuries; cholestatic liver disorders; blood coagulation disorders; metabolic diseases, and others. In the present invention, the liver-related disease may be either inflammatory or non-inflammatory. The adipose tissue-derived multilineage progenitor cells which is contained in a therapeutic agent of the present invention are characterized in that their administration via portal vein results in their differentiation and engraftment with high efficiency also in a non-inflamed liver, and thus has the advantage of being particularly effective for non-inflammatory liver-related diseases. Non-inflammatory liver-related diseases include blood coagulation disorders such as hemophilia, lipid metabolism disorders such as familial hypercholesterolemia, and carbohydrate metabolism disorders such as mucosaccharidosis.

For the purpose of further enhancing therapeutic effects against liver-related diseases according to the present invention, a therapeutic agent of the present invention may be used in combination with other drugs. For example, in cases of the treatment of familial hypercholesterolemia, a therapeutic agent of the present invention may be used in combination with one or more cholesterol-lowering drugs selecting from the group consisting of HMG-CoA reductase inhibitors (so-called statins) such as pravastatin, pitavastatin, and simvastatin; fibrates such as clofibrate, clinofibrate, bezafibrate, and fenofibrate; nicotinate formulations such as tocopherol nicotinate, and nicomol; bile acid adsorbents such as cholestyramine and colestimide; antioxidants such as probucol; cholesterol absorption inhibitors such as ezetimibe, and others, and preferably may be used especially in combination with an HMG-CoA reductase inhibitor such as pravastatin, pitavastatin, and simvastatin. In cases of the treatment of hemophilia, administration of a therapeutic agent of the present invention may be combined with administration of factor VIII or factor IX.

In addition, for the purpose mentioned above, the present invention may be applied to subjects in combination with known therapeutic treatments which are usually administered for liver-related diseases. For example, in cases of the treatment of familial hypercholesterolemia, the present invention may be applied to the subject, for example, in combination with LDL apheresis. Similarly, in cases of the treatment of hemophilia, the present invention may be applied to the subject in combination with replacement therapy with blood coagulation factors, such as factor VIII or factor IX.

Effects of the treatment of liver-related diseases according to the present invention can be determined, for example, by measuring, by means of quantitative PCR, the expression of genes, such as α-fetoprotein, albumin, CYP1B1, glutamine synthetase, keratin-18, and keratin-19, in samples obtained by appropriate procedures, such as biopsy, or alternatively by measuring, by means of quantitative PCR, ELISA, or the like, marker substances, such as transthyretin, α1-antitrypsin, tyrosine aminotransferase, and glucose-6-phosphatase, whose expression are known to decrease or increase in association with differentiation into and generation of hepatocytes. In addition, when a therapeutic agent of the present invention is administered to hemophilia or FH patients, effects may be verified, for example, based on the presence or absence of thrombin produced or on changes in blood cholesterol values after administration.

The present invention, in another aspect, is directed to a method for treating a liver-related disease using adipose tissue-derived multilineage progenitor cells as described herein.

The present invention, in an additional aspect, is directed to use of an adipose tissue-derived multilineage progenitor cell as described herein for manufacturing a therapeutic agent for treating a liver-related disease. The present invention, in still another aspect, is directed to an adipose tissue-derived multilineage progenitor cell as described herein for use in the treatment of a liver-related disease.

Examples are provided below to describe the present invention more specifically and in greater detail, which are described only for illustration, and not intended to limit the present invention. In the examples which follow, differences in average between hADMPC implanted and control groups are evaluated using Student's t-test with an SPSS Statics 17.0 (SPSS).

Example 1

Preparation of Human Adipose Tissue-Derived Multilineage Progenitor Cells (hADMPCs)

1-1. Harvesting of Adipose Tissues

Adipose tissues were harvested from five subjects (four males and one female of from 20 to 60 years old) from whom informed consent had been obtained, according to procedures described in WO2008/153179.

1-2. Preparation of hADMPCs

Harvested adipose tissues were minced, and digested in Hanks' buffer solution (HBSS; GIBCO Invitrogen) containing 0.075% collagenase (Sigma Aldrich) at 37° C. for one hour. The digestion product was filtered through a Cell Strainer (BD Bioscience), followed by centrifugation at 800×g for 10 minutes. Then, a Lymphoprep (d=1.077; Nycomed) was used to remove erythrocytes by a specific-gravity method.

The resultant cells were seeded in DMEM medium (GIBCO Invitrogen) containing 10% fetal bovine serum (FBS; Hyclone). After culturing the cells at 37° C. for one hour and washing adhered cells with PBS, the adhered cells were treated with a 0.2 g/L solution of EDTA (NACLAI TESQUE, INC.) and a population of detached cells was obtained as adipose tissue-derived multilineage progenitor cells (hADMPCs).

1-3. Propagation and Characterization of hADMPCs (1) Propagation of hADMPCs

In human fibronectin-coated dishes (BD BioCoat), hADMPCs obtained in 1-2 were seeded at a density of 10,000 cells/cm$^2$ and cultured in a medium consisting of 60% low glucose DMEM, 40% MCDB-201 (Sigma Aldrich), 1× ITS (GIBCO Invitrogen), 1 nM dexamethasone (Sigma Aldrich), 100 μM ascorbic acid 2-phosphate, 10 ng/ml EGF (Prepro-Tec), and 5% FBS. After 2 to 3 passages, hADMPCs exhibited a single layer structure of flattened cells having diameters of around 25 to 30 μm. In the present invention, hADMPCs which had been passaged five to six times were used for implantation. On hADMPCs used in implantation experiments, expression characterization as described below was performed.

(2) Characterization of the Expression of Cell Surface Antigens

HADMPCs after five to six passages were examined for the expression of ABCG-2, SSEA-4, CD29, CD31, CD34, CD44, CD45, CD73, CD105, CD117, CD133, and CD166, using FACS analysis. The hADMPCs in the present invention were found to express CD29 and CD44 (hyaluronic acid receptor), surface markers which are expressed in mesenchymal or neural stem cells, but not in ES cells, as well as CD73, CD105 (endoglin), and CD166, and additionally SSEA-4. On the other hand, adipose tissue-derived stem cells (hADSCs), which were reported in Mol. Biol. Cell, 13, 4279-4295 (2002), were negative for CD45, which is a marker of the hematopoietic lineage, and for ABCG-2, CD34, and CD133, which are markers of hematopoietic stem cells. From these results, it was ascertained that the hADMPCs in the present invention was a population of cells different from hADSCs.

(3) Characterization of mRNA Expression

HADMPCs after five to six passages were examined for the mRNA expression of islet-1, Nkt2.5, and GATA-4, using RT-PCR analysis. The hADMPCs in the present invention were found to express islet-1, which is an undifferentiation marker, and GATA-4, which is a marker of hepatic progenitor cells, and additionally Nkx2.5. On the other hand, hADSCs were found to express none of islet-1, Nkt2.5, and GATA-4.

(4) Differentiation Capability of hADMPCs into Various Cell Types

With hADMPCs obtained by the above-described procedures, it was found that according to the method described in WO2008/153180, the hADMPCs were differentiation-induced into pancreatic cells (insulin secreting cells), hepatocytes, cardiac myoblasts, adipocytes, or bone tissue, and thus had the capability of differentiating into cells of various lineage tissues (data not shown).

Example 2

Effects of hADMPC Implantation in a Rabbit Model of Familial Hypercholesterolemia 2-1. Implantation of hADMPCs Watanabe heritable hypercholesterolemic rabbits, an animal model for familial hypercholesterolemia (WHHL rabbits; available from KITAYAM LABES Co., Ltd.), were anesthetized with a 50 mg/kg dose of pentobarbital and subjected to incision to the edge of the chest. Subsequently, 5×10$^7$ hADMPCs, obtained in Example 1-3(1), were suspended in 3 mL of HBSS and administered via portal vein using a 24-gauge syringe (hADMPC implanted group). In addition, model rabbits into which HBSS was administered instead of the hADMPC containing suspension in the above protocol were used as a control group for analysis as described below.

2-2. Immunosuppression and Anti-Viral Treatments

In the present invention, rabbits were subjected to immunosuppression and anti-viral treatments according procedures described below, in order to implant human cells in the rabbits. During a period from the preceding day (day −1) of the day when hADMPC implantation was performed (day 0) to the day of sacrifice, each rabbit received intramuscular administrations of cyclosporin (6 mg/kg/day) and rapamycin (0.05 mg/kg/day). Each rabbit received stepwise administrations of methylprednisolone at doses of 3 mg/kg/day (days 1 to 7), 2 mg/kg/day (days 8 to 14), 1 mg/kg/day (days 15 to 21), and 0.5 mg/kg/day (day 22 to the day of sacrifice). Cyclophospamide (20 mg/kg/day) was administered on days 0, 2, 5, and 7. Ganciclovir (2.5 mg/kg/day i.m.) was administered in order to prevent vial infection of the rabbits which became susceptive to infection due to immunosuppression. The control group was also subjected to immunosuppression treatments in a similar way as described above.

2-3. Analysis (1) Lipid Profiling

Quantitative and qualitative changes in serum cholesterol in the hADMPC implanted group were analyzed. With the hADMPC implanted group (n=7), a group in which hADSCs (according to the method of Zuk et. al.) were implanted (n=3), and the control group (n=5), sera were collected from unfasted rabbits before and after the implantation. An assay kit (Wako Pure Chemical Industries, Ltd.) was used to measure total cholesterol in serum up to 12 weeks post-implantation.

As shown in FIG. 1, the hADMPC implanted group has great decrease in total serum cholesterol within three weeks post-implantation and kept a tendency of decreasing the total serum cholesterol throughout the measurement period. The level of total serum cholesterol in a group of WHHL rabbits before the hADMPC implantation was 500 to 800 mg/dL, and at three weeks post-implantation, the group after the hADMPC implantation had a total serum cholesterol of about 400 mg/dL and was found to have a significant decrease in total serum cholesterol, as compared to the control group, which had a total serum cholesterol of about 639 mg/dL.

Figure 2:
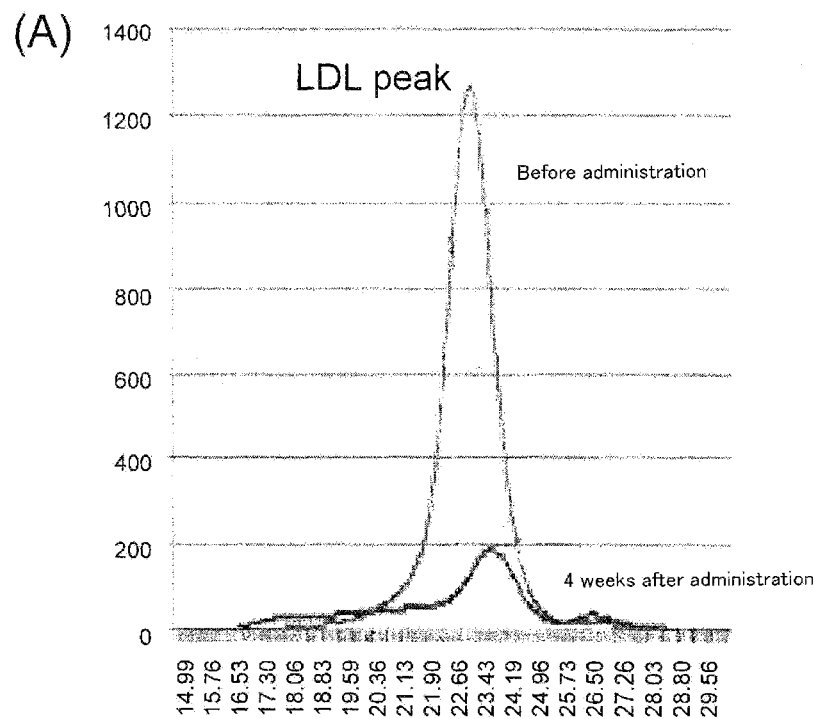
FIG. 2 shows HPLC analysis results of serum cholesterol before and at 4 weeks after the hADMPC implantation.
Figure 2:
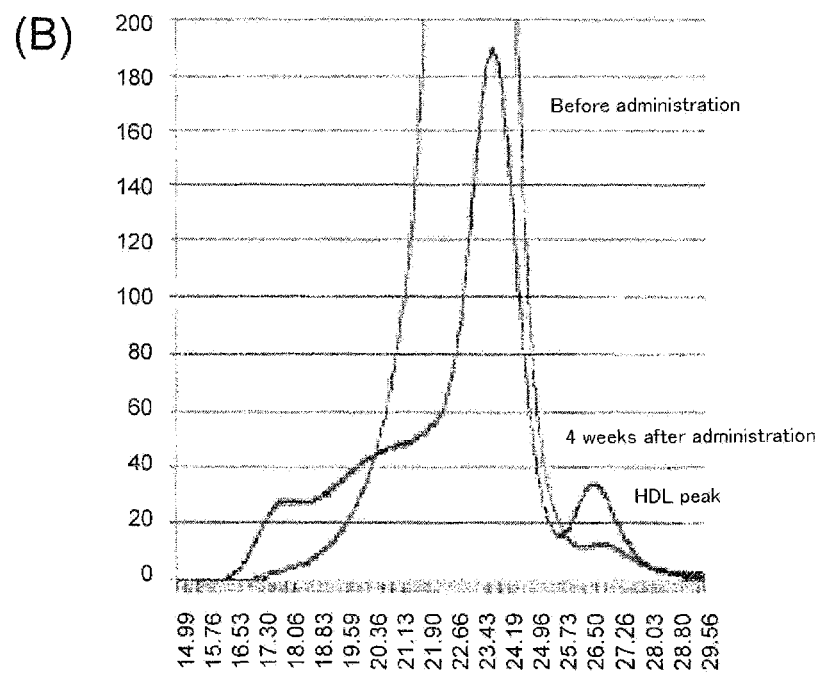

In order to investigate effects of hADMPC implantation on the relative ratio of HDL and LDL, their fractionating was performed using medium/high pressure liquid chromatography (FPLC). The results are shown in FIG. 2. In the figure, the right-sided [sic] panel is shown as a magnified representation of the chromatograms of the left-sided [sic] panel.

As shown in FIG. 2, at four weeks after the hADMPC implantation, the peak of LDL cholesterol was apparently reduced and a fraction of HDL cholesterol was detected. The increase in HDL cholesterol is a phenomenon which is observed after LDL has been decreased by existing therapeutic treatments or when a cDNA for an LDL receptor have been introduced with an adenovirus vector, and is known to reduce the risk of coronary heart diseases.

(2) Ascertainment that Implanted hADMPCs Differentiate into Hepatocytes and are Active In Vivo—1

In order to ascertain that implanted hADMPCs differentiate into hepatocytes in vivo, mRNA expression levels of markers of mature hepatocytes were examined in the livers from the hADMPC implanted group.

WHHL rabbits were implanted with hADMPCs, and sacrificed 12 weeks later, and the liver was removed from each rabbit. Total RNA of each liver was isolated and subjected to quantitative RT-PCT using an ABI Prism 7900 Sequence Detection System (Applied Biosystems), for analysis of the expression of human alpha-1 antitrypsin (hAAT1), human albumin (hAlb), human factor IX (hFactor9), human GATA-4 (hGATA4), human hepatocyte nuclear factor 313 (HNF-3beta), human LDL receptor (hLDL-R), and human glyceraldehyde-3-phosphate dehydrogenase (GAPDH) as markers of mature hepatocytes. In the quantitative RT-PCT, hADMPCs before the implantation were used as control, and the mRNA levels were normalized by GAPDH expression. The TaqMan probes used for these markers are given in Table 1.

TABLE 1

| Gene Name | Assay ID |
|---|---|
| hAAT1 | Hs01097800_m1 |
| hAlb | Hs00609411_m1 |
| hFactor9 | Hs00609168_m1 |
| hGATA4 | Hs00171403_m1 |
| HNF-3beta | Hs00232764_m1 |
| hLDL-R | Hs00181192_m1 |
| hGAPDH | Hs99999905_m1 |

Figure 3:
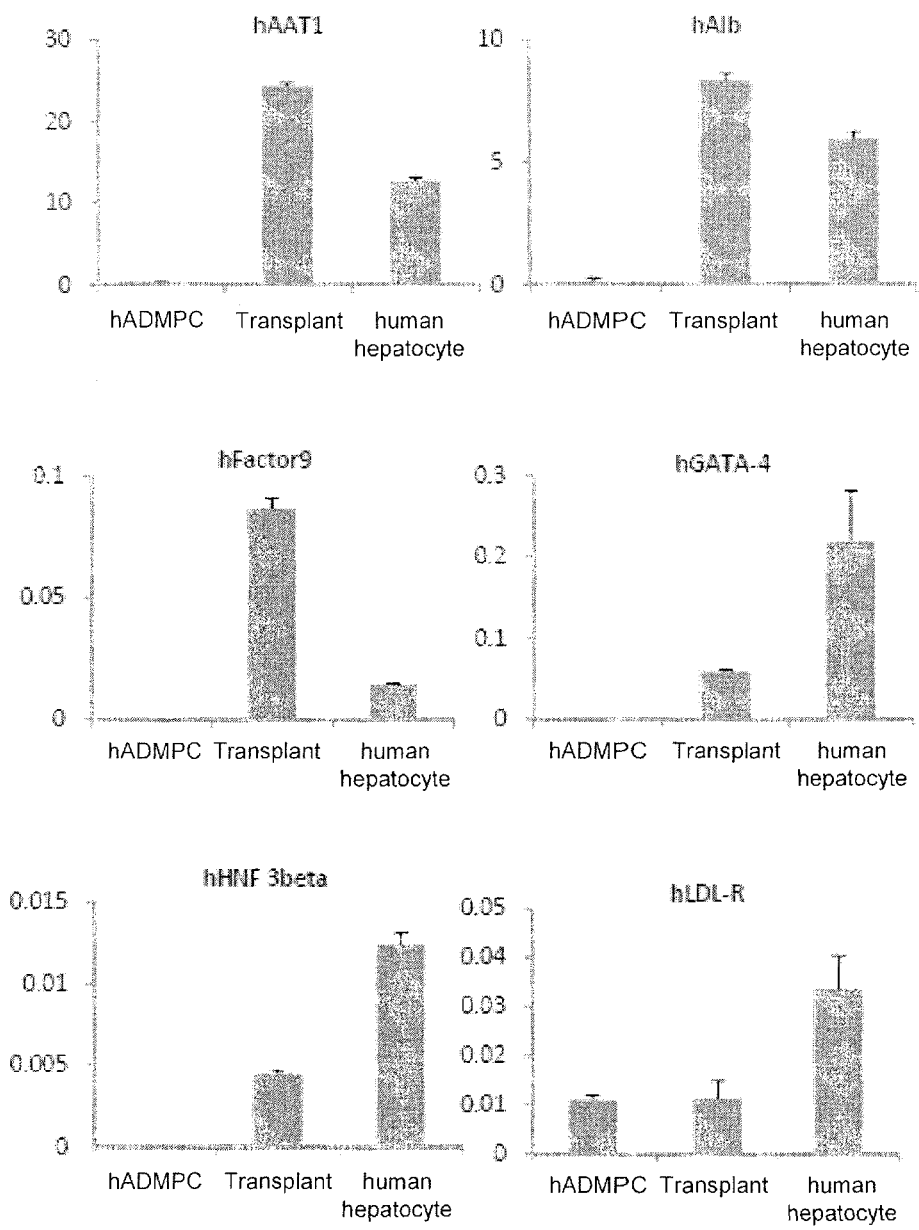
FIG. 3 shows levels of the mRNA expression of various makers in hADMPCs, an hADMPC implanted group, and human hepatocytes. The ordinate axis represents relative values of the mRNA expression level.

The results are shown in FIG. 3. It was ascertained that in hepatocytes from the hADMPC implanted group, markers' mRNAs were expressed at higher levels than in the hADMPCs.

(3) Ascertainment that Implanted hADMPCs Differentiate into Hepatocytes and are Active In Vivo—2

In order to ascertain that implanted hADMPCs differentiate into hepatocytes and function in vivo, the presence of human albumin protein in sera from the hADMPC implanted group was analyzed according to conventional procedures using immunoblot and ELISA.

Immunoblotting of sera before the hADMPC implantation verified that the anti-human specific albumin antibody used in this experiment (goat polyclonal, bovine, mouse and pig ALB-ads orbed, affinity purified; Bethyl Laboratories) did not detect rabbit serum albumin.

ELISA results showed that human serum albumin was detected at three weeks post-implantation and expressed during the subsequent period of analysis. The fact that human albumin was observed to be produced in the hADMPC implanted group implies that surviving and functioning hepatocytes derived from ADMPCs are present.

(4) Ascertainment that hADMPCs Migrate into Hepatic Parenchyma, Differentiate into Hepatocytes, and Function In order to ascertain that hADMPCs differentiate into hepatocytes at appropriate locations, sections of the livers from the hADMPC implanted group were subjected to histochemical analysis.

As a tracer was used DiO (3,3'-dioctadecyloxacarbocyanine perchlorate; Sigma Aldrich). DiO pretreated hADMPCs (DiO-hADMPCs) were implanted in WHHL rabbits via portal vein. One week post-implantation, the rabbits were sacrificed, and tissue sections prepared were observed under a fluorescence microscope. DiO-hADMPCs were localized at sites around the portal vein, and in one week post-implantation, migrated, with morphological changes, into the hepatic parenchyma in the direction of the center of hepatic lobules.

WHHL rabbits were implanted with hADMPCs via portal vein and sacrificed 12 weeks later. The liver was removed from each rabbit and fixed in 10% formalin, and frozen sections prepared were immunostained with anti-human albumin and anti-LDL receptor antibodies.

Figure 4:
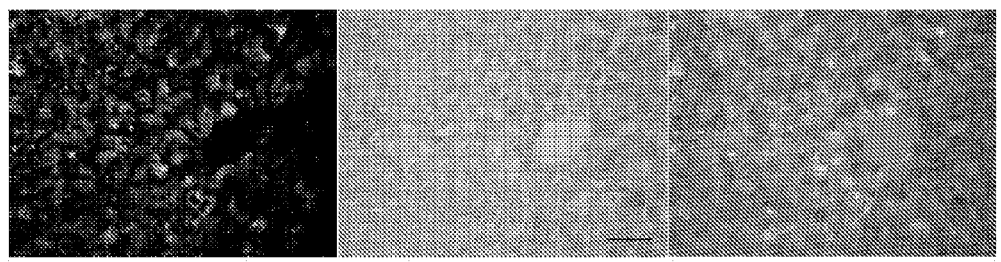
FIG. 4 shows the expression of human albumin in livers in an hADMPC implanted group. In the figure, the bar represents 100 μm.
Figure 5:
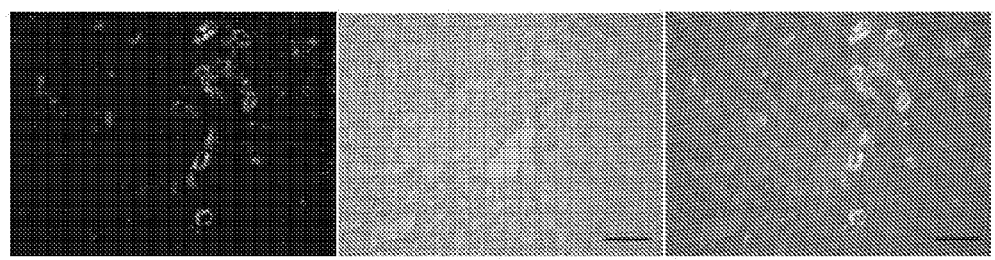
FIG. 5 shows the expression of LDL receptor in livers in an hADMPC implanted group. In the figure, each of the bars represents 100 μm.

Results using these antibodies are shown in FIGS. 4 and 5, respectively. When observed under a fluorescence microscope, cells which were positive for human albumin and LDL receptor were found to be present in dispersion, contacting with and integrating with host cells around hepatic parenchymal veins. The presence of cells positive for human albumin verified that implanted hADMPCs differentiated into hepatocytes, and these hepatocytes being positive for LDL receptor verified that the differentiated cells were active.

It is believed that native hepatocytes migrate from the portal vein toward the center of hepatic lobules. The migration of hADMPCs and the presence of hADMPC derived hepatocytes in the livers of WHHL rabbits are in agreement with this model. It has also been shown that signals in the interaction between hepatocytes or between hypatocytes and matrices are kept between hADMPC derived hepatocytes and affected hepatocytes (WHHL rabbits).

(5) In Vitro Uptake of LDL by hADMPC Derived Hepatocytes

In order to ascertain the in vitro uptake of LDL by hADMPC derived hepatocytes, sections of the livers from the hADMPC implanted group were subjected to histochemical analysis.

Human LDL (density of 1.019 to 1.063 g/ml) was isolated from a donor's blood with normal blood lipid, by sequential procedures of ultracentrifugation, dialysis in saline-EDTA, and sterilization by filtration through a 0.2 .mu.m filter, and then labeled with DiO to prepare DiO-LDL. WHHL rabbits were implanted with hADMPCs via portal vein, and sacrificed 12 weeks later. Tissue sections of the livers removed were prepared and then incubated in serum-free DMEM medium containing 10 .mu.g/mL DiO-LDL at 37.degree. C. for 24 hours. After washing, the sections were fixed in 10% formalin, cut at a thickness of 5 .mu.m, mounted on PERMA-FLUOR™ apparatus (JAPAN TANNER CORPORATION), and analyzed using a BioZero laser scanning microscope (KEYENCE CORPORATION) to determine the in vitro uptake of DiO-LDL by the implanted cells.

Figure 6:
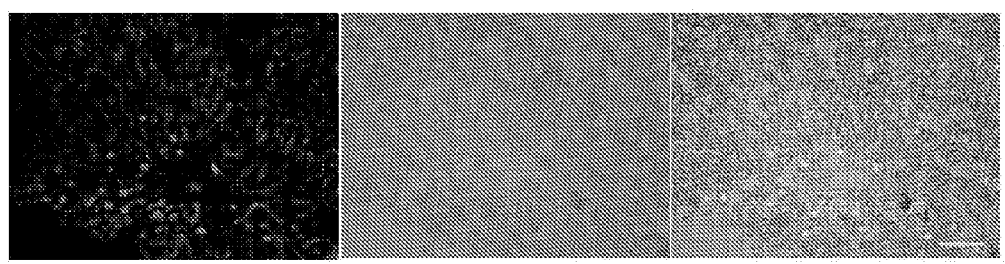
FIG. 6 shows the uptake of LDL in livers in an hADMPC implanted group. In the figure, the bar represents 100 μm.

Results are shown in FIG. 6, which indicates that DiO-LDL was incorporated by some, but not all, of the implanted hADMPCs. The cells incorporating DiO-LDL were found to be present in dispersion, contacting with and integrating with hepatic parenchymal cells not incorporating DiO-LDL. From this, it is suggested that hADMPCs differentiate into hepatocytes in vivo and reduce serum cholesterol through the uptake of LDL, whereby patients with familial hypercholesterolemia can be treated.

(6) Clearance Rate of Blood LDL in hADMPC Implanted Group

In order to ascertain the metabolism of LDL in an hADMPC implanted group, sera collected from the rabbits in the hADMPC implanted group were analyzed.

WHHL rabbits (eight weeks old, available from KITAYAM LABES Co., Ltd.) were anesthetized with pentobarbital (50 mg/kg), subjected to peritoneum incision, and administered via portal vein with hADMPCs suspended in HBSS (20° C.) ($3\times10^7$ cells/rabbit high-dose subgroup, n=2; $5\times10^6$ cells/rabbit for a low-dose subgroup, n=2) or with saline (3 ml), using 18-gause syringes (hADMPC implanted group (n=5) and control (n=2) group, respectively). Each rabbit was subjected to immunosuppression as in Example 2-2 and to LDL metabolic assay at 8 weeks. [I-125]-human LDL (Biomedical Technologies Inc.) was suspended in saline containing 2 mg/ml bovine serum albumin and administered via ear vein in the hADMPC implanted group and control group. At specified times elapsing from the administration (5 minutes, 1 hour, 2 hours, 4 hours, 6 hours, and 28 hours, for each group), blood was collected in the opposite ear. Twenty-percent trichloroacetic acid (Wako Pure Chemical Industries, Ltd.) (320 µl of serum, 80 µl of 100% w/v TCA) was used to precipitate LDL including $^{125}$I-labeled apolipoprotein B, and the resulting precipitate was subjected to scintillation measurement.

Figure 7:
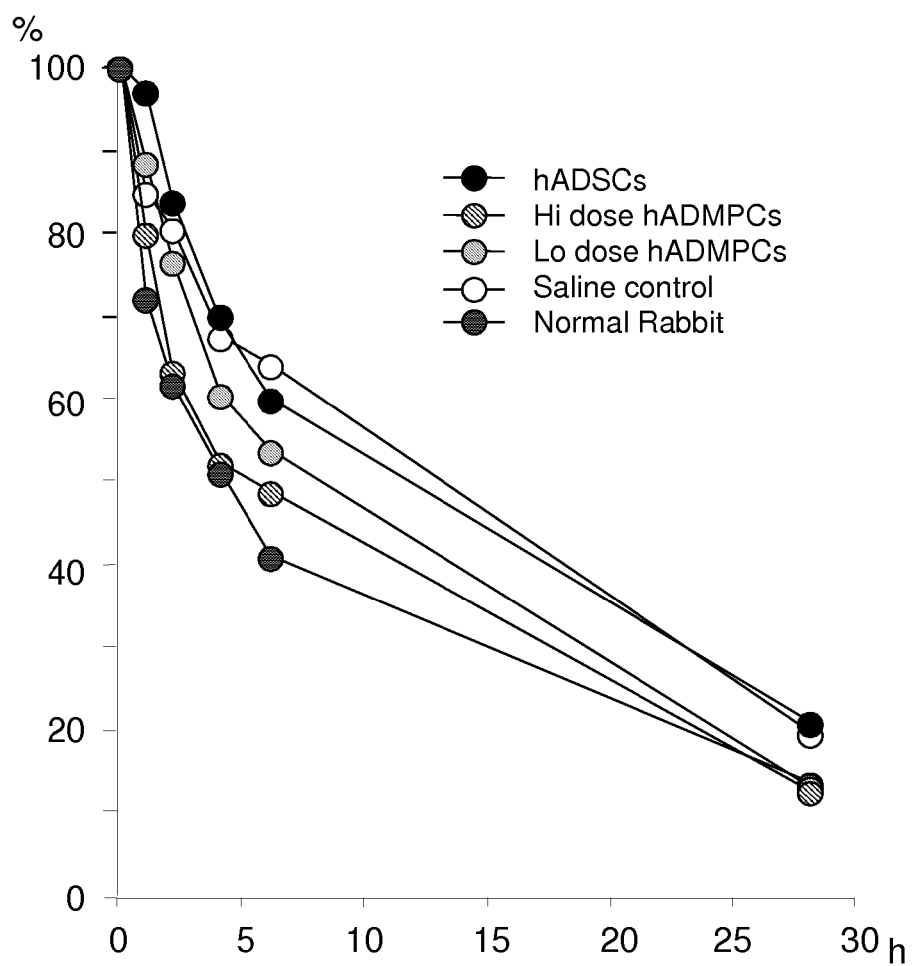
FIG. 7 shows changes in values of blood cholesterol in an hADSC implanted group, an hADMPC implanted group, a saline control group, and normal rabbits. In the graph, the abscissa axis represents elapsed days and the ordinate axis represents values of blood cholesterol.

The results are shown in FIG. 7. The rate of clearance of LDL in the hADMPC implanted group was 2.4 times (for the high-dose subgroup) and 1.4 times (for the low-dose subgroup), as compared to that in the control group in which hADMPCs were not implanted (saline control), and there was observed a significant increase in the rate of clearance of LDL in the hADMPC implanted group. In particular, the high-dose hADMPC implanted sub-group had the same rate of clearance as that in normal rabbits. The hADMPC implanted group also had a significant increase in the rate of clearance of LDL, as compared to the hADSC implanted group.

INDUSTRIAL APPLICABILITY

The present invention can provide, for example, a therapeutic agent for treating a liver-related disease, which includes adipose tissue-derived multilineage progenitor cells that exhibit increased engraftment and differentiation in the liver when introduced in the body. In addition, the present invention makes it possible to treat refractory diseases, such as hemophilia and familial hypercholesterolemia, with reduced physical and economic burdens on patients.

The invention claimed is:

1. A method for treating a liver-related disease, comprising:
    administering adipose tissue-derived multilineage progenitor cells to a subject,
    wherein the adipose tissue-derived multilineage progenitor cells are a population of cells obtained by:
    (a) removing erythrocytes from a population of adipose tissue-derived cells, thereby to form a population of preadipose tissue-derived multilineage progenitor cells;
    (b) culturing the resultant population of the preadipose tissue-derived multilineage progenitor cells;
    (c) removing cells other than the adipose tissue-derived multilineage progenitor cells using ethylenediaminetetraacetic acid (EDTA) and without using trypsin.

2. The method according to claim 1, wherein adipose tissue-derived multilineage progenitor cells are administered via portal vein.

3. The method according to claim 1, wherein the liver-related disease is non-inflammatory.

4. The method according to claim 3, wherein the liver-related disease is hemophilia or familial hypercholesterolemia.

5. The method according to claim 1, wherein the liver-related disease is selected from blood coagulation disorders, metabolic diseases, and liver diseases.

* * * * *